(12) United States Patent
Thirumalai Rajan et al.

(10) Patent No.: US 9,718,779 B2
(45) Date of Patent: Aug. 1, 2017

(54) INTERMEDIATE AND POLYMORPHS OF 1-(4-METHOXYPHENY1)-7-OXO-6-[4-(2-OXOPIPERIDIN-1-YL)PHENYL]-4,5,6,7-TETRA HYDRO-1H-PYRAZOLO[3,4-C] PYRIDINE-3-CARBOXAMIDE AND PROCESS THEREOF

(71) Applicant: MSN LABORATORIES LIMITED, Hyderabad (IN)

(72) Inventors: Srinivasan Thirumalai Rajan, Hyderabad (IN); Sajja Eswaraiah, Hyderabad (IN); Mummadi Venkatesh, Hyderabad (IN)

(73) Assignee: MSN Laboratories Limited (IN)

( * ) Notice: Subject to any disclaimer, the term of this patent is extended or adjusted under 35 U.S.C. 154(b) by 26 days.

(21) Appl. No.: 14/759,712

(22) PCT Filed: Jan. 8, 2014

(86) PCT No.: PCT/IN2014/000019
§ 371 (c)(1),
(2) Date: Jul. 8, 2015

(87) PCT Pub. No.: WO2014/108919
PCT Pub. Date: Jul. 17, 2014

(65) Prior Publication Data
US 2015/0353541 A1    Dec. 10, 2015

(30) Foreign Application Priority Data
Jan. 9, 2013   (IN) .............. 136/CHE/2013

(51) Int. Cl.
*C07D 471/04*    (2006.01)
*C07D 211/40*    (2006.01)
*C07D 211/86*    (2006.01)
*C07C 231/02*    (2006.01)
*C07D 211/76*    (2006.01)
*C07C 249/16*    (2006.01)

(52) U.S. Cl.
CPC .......... *C07D 211/86* (2013.01); *C07C 231/02* (2013.01); *C07C 249/16* (2013.01); *C07D 211/76* (2013.01); *C07D 471/04* (2013.01); *C07B 2200/13* (2013.01)

(58) Field of Classification Search
CPC .. C07D 401/12; C07D 401/14; C07D 413/14; C07D 417/02; C07D 417/14; C07D 471/04; C07D 211/40
USPC ......... 546/169, 187, 216, 243, 277.1, 280.4, 546/300, 113; 544/143, 361, 363, 383, 544/405
See application file for complete search history.

(56) References Cited

U.S. PATENT DOCUMENTS

| 3,068,248 | A | 11/1962 | Camerino et al. |
| 7,396,932 | B2* | 7/2008 | Shapiro ............... C07D 471/04 546/120 |
| 2003/0191115 | A1 | 10/2003 | Pinto et al. |
| 2006/0069258 | A1 | 3/2006 | Shapiro et al. |
| 2010/0130543 | A1* | 5/2010 | Gant .................... C07D 471/04 514/303 |

FOREIGN PATENT DOCUMENTS

IN    4558CHE2012    * 11/2012

OTHER PUBLICATIONS

Goverdhan et al. "process for prepar . . . ." CA163:257825 (2014).*
Goverdhan et al. "Process for preparation . . . . " CA163: 257825Casreact (2014).*
"Electrophilic aromatic dirrecting groups" Wikipedia, p. 1-4 (2017).*
International Search Report for PCT/IN2014/000019 dated Jun. 6, 2014.
IPCOM000216217 "Solid State Forms of Apixaban" URL: http://ip.com/IPCOM/000216217 published on Mar. 25, 2012.
"Crystalline Polymorphism of Organic Compounds" Topic in Current Chemistry, Springer, Berlin DE, vol. 198, Jan. 1, 1998, pp. 163-208.

* cited by examiner

*Primary Examiner* — Celia Chang
(74) *Attorney, Agent, or Firm* — Caesar Rivise, PC

(57) ABSTRACT

The present invention provides a novel intermediate as well as novel polymorphs of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound represented by the following structural formula-1 and processes for their preparation.

15 Claims, 3 Drawing Sheets

INTERMEDIATE AND POLYMORPHS OF 1-(4-METHOXYPHENY1)-7-OXO-6-[4-(2-OXOPIPERIDIN-1-YL)PHENYL]-4,5,6,7-TETRA HYDRO-1H-PYRAZOLO[3,4-C] PYRIDINE-3-CARBOXAMIDE AND PROCESS THEREOF

RELATED APPLICATIONS

This application claims the benefit of priority of our Indian patent application number 136/CHE/2013 filed on 9 Jan. 2013 which is incorporated herein by reference.

FIELD OF THE INVENTION

The present invention provides novel polymorphs of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound represented by the following structural formula-1 and processes for their preparation.

Formula-1

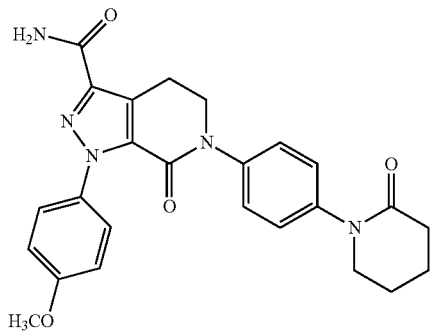

The present invention also provides novel intermediate compound useful for the preparation of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1.

BACKGROUND OF THE INVENTION 1-(4-methoxyphenyl)-7-oxo-6-[4-(2-oxopiperidin-1-yl) phenyl]-4,5,6,7-tetrahydro-1H-pyrazolo[3,4-c]pyridine-3-carboxamide, commonly known as Apixaban (BMS-562247-01) is an anticoagulant for the prevention of venous thromboembolism and venous thromboembolic events. Apixaban is marketed under the trade name "Eliquis" and is being developed in a joint venture by Pfizer and Bristol-Myers squibb.

Lactam containing compounds, their derivatives and process for their preparation was first disclosed in U.S. Pat. No. 6,967,208B2. The disclosed process involves the usage of 1-(4-iodophenyl)-3-morpholino-5,6-dihydropyridin-2(1H)-one (2) (herein after referred as "morpholine substituted lactam compound") an intermediate for the preparation of Apixaban. The preparation of said morpholine substituted lactam compound is represented below:

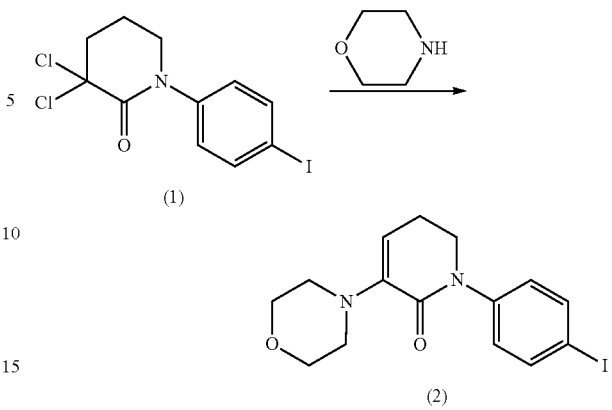

The above said process involves the preparation of compound (2) by condensing the compound (1) with morpholine which involves the use of an excess amount of morpholine. When the above said reaction was repeated in the laboratory, it was found that an excess amount of morpholine is consumed, and apart from this the yields and purity of compound (2) were found to be very low. This can be attributed to the use of excess morpholine which leads to the formation of di-morpholine substituted compound as a by-product. Moreover, the conversion of di-morpholine substituted compound into mono-morpholine substituted compound (2) is a tedious task thereby increasing the cost of the production. Hence the said process is not suitable for the commercial level process.

In order to overcome this, a process involving a novel intermediate (which contains only one chlorine atom) was developed which during condensation avoids the consumption of excess morpholine to provide compound (2).

Crystalline solvates DMF-5 and FA-2 of Apixaban are disclosed in US2007203178A1; the crystalline forms N-1 and H2-2 of Apixaban are disclosed in U.S. Pat. No. 7,396,932B2; and the crystalline forms-I and II of Apixaban are disclosed in IPCOM000216217D.

The crystalline or polymorphic form may give rise to thermal behavior different from that of the amorphous material or another crystalline or polymorphic form. Thermal behavior is measured in the laboratory by such techniques as capillary melting point, thermogravimetric analysis (TGA) and differential scanning calorimetry (DSC) and may be used to distinguish some crystalline or polymorphic forms from others. A particular crystalline or polymorphic form may also give rise to distinct spectroscopic properties that may be detectable by X-ray powder diffraction (XRPD), solid state nuclear magnetic resonance (NMR) spectrometry, Raman spectroscopy and infrared (IR) spectrometry.

In deciding which polymorph or crystalline form is preferable, the numerous properties of the polymorphs or crystalline forms must be compared and the preferred polymorph or crystalline form chosen based on the many physical property variables. It is entirely possible that one polymorph or crystalline form can be preferable in some circumstances in which certain aspects, such as ease of preparation, stability, etc., are deemed to be critical. In other situations, a different crystalline form or polymorph may be preferred for greater solubility and/or superior pharmacokinetics.

The discovery of new crystalline or polymorphic forms of active pharmaceutical ingredient always provides a new opportunity to improve the performance characteristics of a desired pharmaceutical product.

The present inventors have developed novel crystalline forms which have greater free flow characteristics, consistently reproducible and suitable for the pharmaceutical formulations.

BRIEF DESCRIPTION OF THE INVENTION

The first aspect of the present invention is to provide 3-chloro-1-(4-iodophenyl)-5,6-dihydropyridin-2(1H)-one compound of formula-6, which is an useful intermediate in the synthesis of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1.

Further, the first aspect of the present invention also provides a process for the preparation of 3-chloro-1-(4-iodophenyl)-5,6-dihydropyridin-2(1H)-one compound of formula-6.

The second aspect of the present invention is to provide a process for the preparation of 1-(4-iodophenyl)-3-morpholino-5,6-dihydropyridin-2(1H)-one compound of formula-7, comprising of reacting the 3-chloro-1-(4-iodophenyl)-5,6-dihydropyridin-2(1H)-one compound of formula-6 with morpholine in presence or absence of a suitable solvent to provide 1-(4-iodophenyl)-3-morpholino-5,6-dihydropyridin-2(1H)-one compound of formula-7.

The third aspect of the present invention is to provide a novel process for the preparation of ethyl 6-(4-iodophenyl)-1-(4-methoxyphenyl)-7-oxo-4,5,6,7-tetrahydro-1H-pyrazolo[3,4-c]pyridine-3-carboxylate compound of formula-13, comprising of reacting the 3-chloro-1-(4-iodophenyl)-5,6-dihydropyridin-2(1H)-one compound of formula-6 with (Z)-ethyl 2-chloro-2-(2-(4-methoxyphenyl)hydrazono)acetate compound of formula-9 in presence of a suitable base in a suitable solvent to provide ethyl 6-(4-iodophenyl)-1-(4-methoxyphenyl)-7-oxo-4,5,6,7-tetrahydro-1H-pyrazolo[3,4-c]pyridine-3-carboxylate compound of formula-13.

The fourth aspect of the present invention is to provide a novel crystalline form of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1 (herein designated as crystalline form-M) and process for its preparation.

The fifth aspect of the present invention is to provide a novel crystalline form of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1 (herein designated as crystalline form-S) and process for its preparation.

The sixth aspect of the present invention is to provide a novel crystalline form of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1 (herein designated as crystalline form-N) and process for its preparation.

The seventh aspect of the present invention is to provide a process for the preparation of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1.

The eighth aspect of the present invention is to provide a process for the preparation of ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate compound of formula-11.

DETAILED DESCRIPTION OF THE INVENTION

Figure 1:
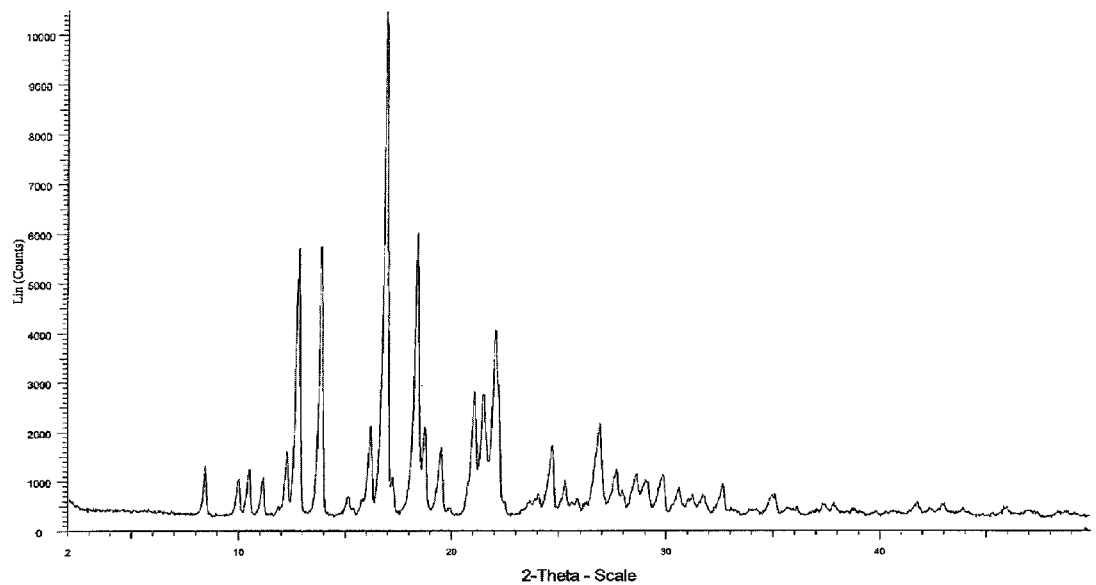
FIG. 1: Illustrates the powder X-Ray diffraction pattern of crystalline form-M of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1.

As used herein the present invention the term "suitable solvent" refers to "hydrocarbon solvents" such as n-hexane, n-heptane, cyclohexane, pet.ether, toluene, xylene and the like; "chloro solvents" such as dichloromethane, dichloroethane, carbon tetrachloride, chloroform and the like; "ester solvents" such as methyl acetate, ethyl acetate, propyl acetate, isopropyl acetate and the like; "polar aprotic solvents" such as dimethyl acetamide, dimethyl formamide, dimethyl sulfoxide and the like; "nitrile solvents" such as acetonitrile, propionitrile, isobutyronitrile and the like; "ether solvents" such as dimethyl ether, diethyl ether, isopropyl ether, diisopropyl ether, methyl tert-butyl ether, 1,2-dimethoxy ethane, tetrahydrofuran, dioxane and the like; "alcoholic solvents" such as methanol, ethanol, propanol, isopropanol, n-butanol, isobutanol, tert-butanol and the like; "ketone solvents" such as acetone, propanone, methyl ethyl ketone, methylisobutyl ketone, methylisopropyl ketone and the like; and "polar solvents" such as water; and/or their mixtures thereof.

The term "suitable base" used herein the present invention refers, but not limited to "inorganic bases" selected from alkali and alkaline earth metal hydroxides, alkoxides, carbonates and bicarbonates such as sodium hydroxide, potassium hydroxide, lithium hydroxide, sodium methoxide, sodium ethoxide, potassium methoxide, sodium tert-butoxide, potassium tert-butoxide, lithium tert.butoxide, lithium carbonate, sodium carbonate, potassium carbonate, lithium bicarbonate, sodium bicarbonate, potassium bicarbonate and the like; alkali metal hydrides such as sodium hydride, potassium hydride, lithium hydride and the like; alkali metal amides such as sodium amide, potassium amide, lithium amide and the like, ammonia; and organic bases like dimethylamine, diethylamine, diisopropyl amine, diisopropylethylamine, diisobutylamine, triethylamine, pyridine, 4-dimethylaminopyridine (DMAP), N-methyl morpholine (NMM), 2,6-lutidine, lithium diisopropylamide; organosilicon bases such as lithium hexamethyldisilazide (LiHMDS), sodium hexamethyldisilazide (NaHMDS), potassium hexamethyldisilazide (KHMDS) and/or their mixtures thereof.

The term "alkali metal halide" used herein the present invention refers to lithium chloride, sodium chloride and the like.

The term "suitable acid" used herein the present invention refers to hydrochloric acid, hydrobromic acid, sulfuric acid and nitric acid.

The main object of the present invention is to avoid the usage of excess amount of morpholine. In view of this, the present inventors have developed a process for the preparation of morpholine substituted lactam compound of formula-7 which proceeds through a novel intermediate i.e., 3-chloro-1-(4-iodophenyl)-5,6-dihydro pyridin-2(1H)-one. The usage of said novel intermediate not only avoids the formation of di-morpholine substituted compound of formula-7 but also avoids the usage of excess amount of morpholine thereby increases the yield and purity of the desired compound of formula-7.

The first aspect of the present invention provides 3-chloro-1-(4-iodophenyl)-5,6-dihydropyridin-2(1H)-one compound of formula-6,

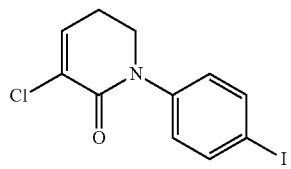

Formula-6 which is an useful intermediate in the synthesis of 1-(4-methoxyphenyl)-7-oxo-6-[4-(2-oxopiperidin-1-yl)phenyl]-4,5,6,7-tetrahydro-1-H-pyrazolo[3,4-c]pyridine-3-carboxamide compound of formula-1.

Further, the first aspect of the present invention also provides a process for the preparation of 3-chloro-1-(4-iodophenyl)-5,6-dihydropyridin-2(1H)-one compound of formula-6, comprising of treating the 3,3-dichloro-1-(4-iodophenyl)piperidin-2-one compound of formula-5

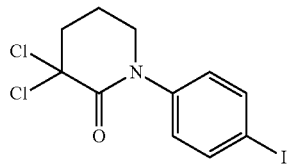

Formula-5 with lithium carbonate in presence of alkali metal halides such as lithium chloride, sodium chloride in a suitable solvent at a suitable temperature to provide 3-chloro-1-(4-iodophenyl)-5,6-dihydropyridin-2(1H)-one compound of formula-6.

Wherein, the "suitable solvent" employed is selected from hydrocarbon solvents, chloro solvents, ester solvents, ether solvents, alcoholic solvents, ketone solvents, polar aprotic solvents, polar solvents and/or mixtures thereof; preferably polar aprotic solvents;

"lithium carbonate" and the "alkali metal halide" are employed individually in molar proportions ranging from 0.2 to 1 equivalents per one mole of compound of formula-5; the "suitable solvent" is employed in an amount ranging from 2 to 10 volumes per 1 gm of compound of formula-5; and the suitable temperature is ranging from 0° C. to 130° C.

The 3,3-dichloro-1-(4-iodophenyl)piperidin-2-one compound of formula-5 which is used as a starting material in the first aspect of the present invention is commercially available or it can be synthesized by any of the methods known in the art.

The second aspect of the present invention provides a process for the preparation of 1-(4-iodophenyl)-3-morpholino-5,6-dihydropyridin-2(1H)-one compound of formula-7

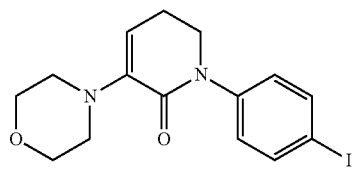

Formula-7 comprising of reacting the 3-chloro-1-(4-iodophenyl)-5,6-dihydropyridin-2(1H)-one compound of formula-6 with morpholine in presence or absence of a suitable solvent at a suitable temperature to provide 1-(4-iodophenyl)-3-morpholino-5,6-dihydropyridin-2(1H)-one compound of formula-7.

Wherein, the "suitable solvent" employed is selected from hydrocarbon solvents, chloro solvents, ester solvents, ether solvents, alcoholic solvents, ketone solvents, polar aprotic solvents, polar solvents and/or mixtures thereof; preferably hydrocarbon solvents and ether solvents;

the "morpholine" is employed in molar proportions ranging from 1 to 10 equivalents per one mole of compound of formula-6; the "suitable solvent" is employed in an amount ranging from 1 to 10 volumes per 1 gm of compound of formula-6; and the suitable temperature is ranging from 0° C. to 140° C.

The 1-(4-iodophenyl)-3-morpholino-5,6-dihydropyridin-2(1H)-one compound of formula-7 obtained in the second aspect of the present invention can be further utilized in the synthesis of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1.

The third aspect of the present invention provides a novel process for the preparation of ethyl 6-(4-iodophenyl)-1-(4-methoxyphenyl)-7-oxo-4,5,6,7-tetrahydro-1H-pyrazolo[3,4-c]pyridine-3-carboxylate compound of formula-13,

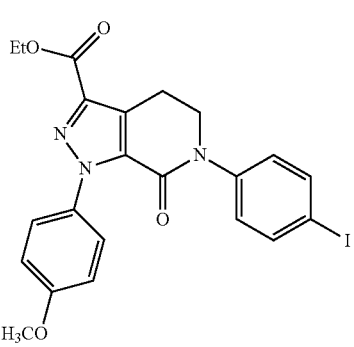

Formula-13 comprising of reacting the 3-chloro-1-(4-iodophenyl)-5,6-dihydropyridin-2(1H)-one compound of formula-6 with (Z)-ethyl 2-chloro-2-(2-(4-methoxyphenyl)hydrazono)acetate compound of formula-9

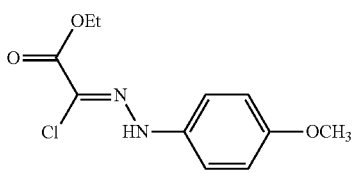

Formula-9 in presence of a suitable base in a suitable solvent at a suitable temperature to provide ethyl 6-(4-iodophenyl)-1-(4-methoxyphenyl)-7-oxo-4,5,6,7-tetrahydro-1H-pyrazolo[3,4-c]pyridine-3-carboxylate compound of formula-13.

Wherein, the "suitable solvent" employed is selected from hydrocarbon solvents, chloro solvents, ester solvents, ether solvents, alcoholic solvents, ketone solvents, polar aprotic solvents, polar solvents and/or mixtures thereof; the "suitable base" is inorganic base or organic base, The "suitable base" is employed in molar proportions ranging from 1 to 3 equivalents per one mole of compound of formula-6; the "suitable solvent" employed is in an amount ranging from 2 to 10 volumes per 1 gm of compound of formula-6; and the suitable temperature is ranging from 0° C. to 100° C.

The (Z)-ethyl 2-chloro-2-(2-(4-methoxyphenyl)hydrazono)acetate compound of formula-9, which is used as a starting material in the third aspect of the present invention is commercially available or it can be prepared by any of the prior known methods.

The ethyl 6-(4-iodophenyl)-1-(4-methoxyphenyl)-7-oxo-4,5,6,7-tetrahydro-1H-pyrazolo[3,4-c]pyridine-3-carboxylate compound of formula-13 obtained by the process disclosed in the third aspect of the present invention can be further converted to 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1 by using the conventional methods known in the art.

Figure 2:
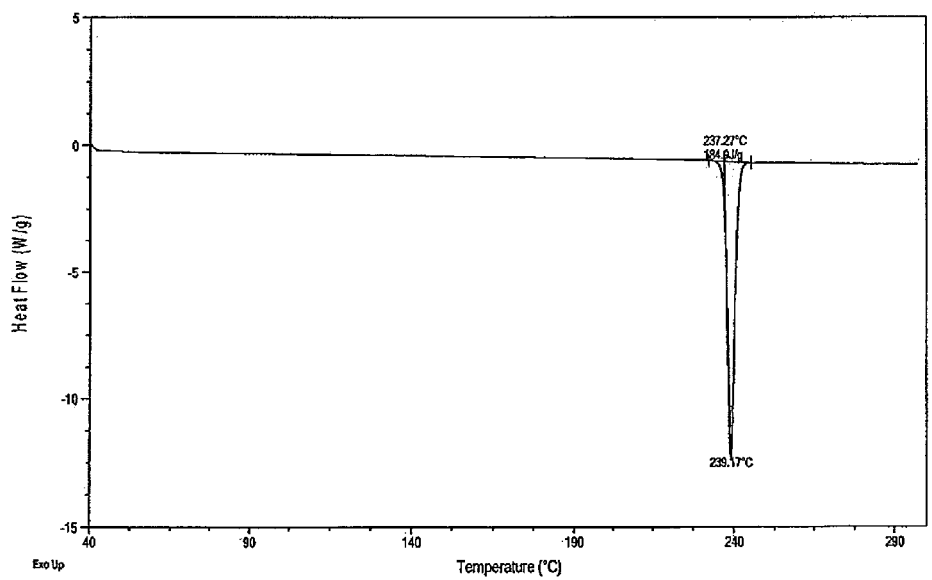
FIG. 2: Illustrates the DSC thermogram of crystalline form-M of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1.

The fourth aspect of the present invention provides a novel crystalline form-M of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1, characterized by;
a) its PXRD pattern substantially in accordance with FIG. 1,
b) its powder X-Ray diffractogram having peaks at 12.7, 13.8, 16.9, 18.4, 22.0, 26.9, 29.0 and 32.7±0.2 degrees of two-theta, and
c) its DSC thermogram as illustrated in FIG. 2.

The fourth aspect of the present invention also provides a process for the preparation of crystalline form-M of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1, comprising the following steps of:
a) Adding isopropanol to 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1,
b) heating the reaction mixture,
c) cooling the reaction mixture,
d) filtering the compound and drying to get crystalline form-M of compound of formula-1.

The fourth aspect of the present invention also provides another process for the preparation of crystalline form-M of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1, comprising the following steps of:
a) Adding aqueous isopropanol to 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1,
b) heating the reaction mixture,
c) cooling the reaction mixture,
d) filtering the compound and drying to get crystalline form-M of compound of formula-1.

Figure 3:
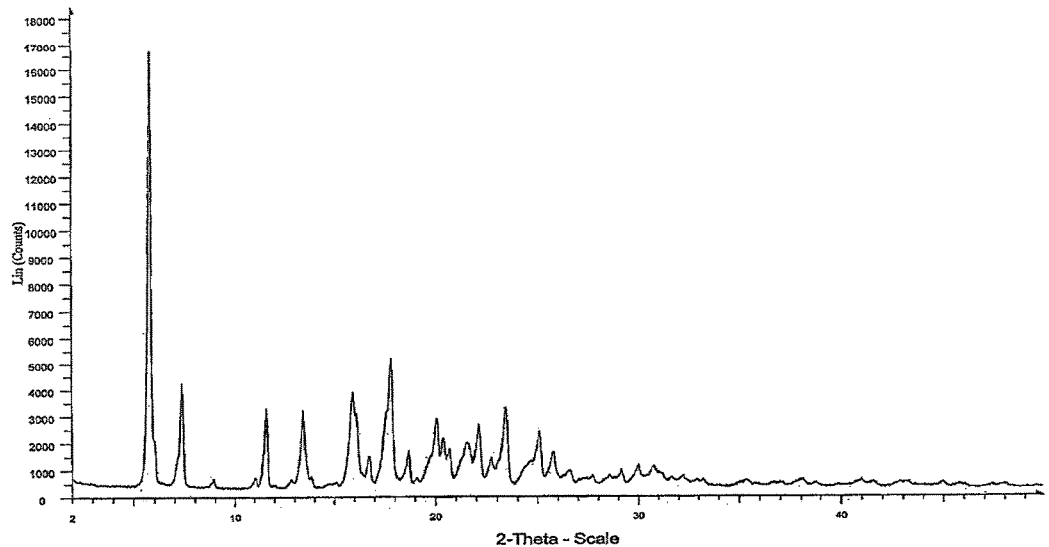
FIG. 3: Illustrates the powder X-Ray diffraction pattern of crystalline form-S of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1.
Figure 4:
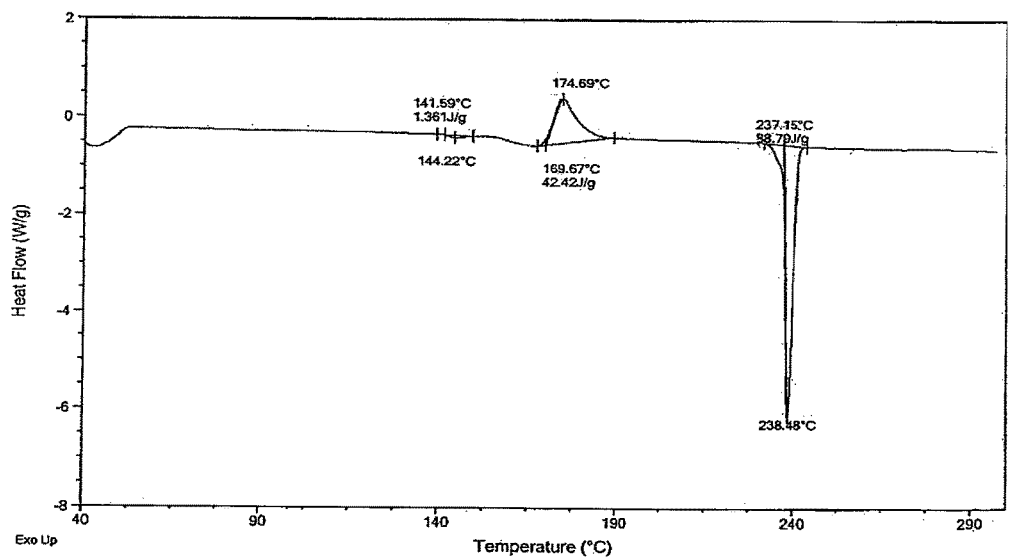
FIG. 4: Illustrates the DSC thermogram of crystalline form-S of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1.

The fifth aspect of the present invention provides a novel crystalline form-S of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1, characterized by;
a) its PXRD pattern substantially in accordance with FIG. 3,
b) its powder X-ray diffractogram having peaks at 5.7, 7.3, 11.5, 13.4, 15.9, 17.5, 17.8, 20.0, 22.1, 23.4 and 25.1±0.2 degrees of two-theta, and
c) its DSC thermogram as illustrated in FIG. 4.

The fifth aspect of the present invention also provides a process for the preparation of crystalline form-S of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1, comprising the following steps of:
a) Dissolving the 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1 in a mixture of dichloromethane and methanol by heating,
b) filtering the reaction mixture,
c) cooling the filtrate obtained in step-b),
d) filtering the precipitated solid and drying to get crystalline form-S of compound of formula-1.

Figure 5:
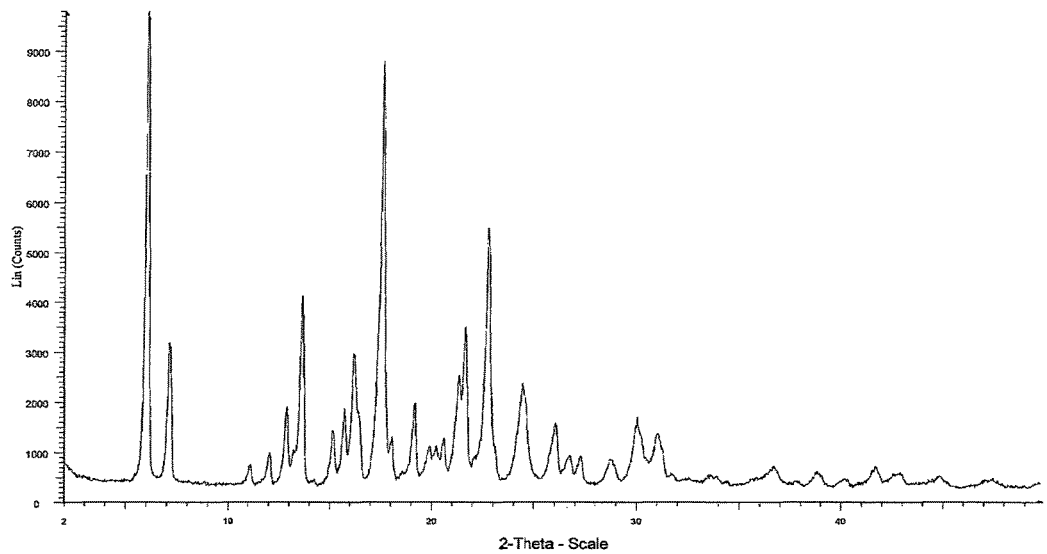
FIG. 5: Illustrates the powder X-Ray diffraction pattern of crystalline form-N of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1.
Figure 6:
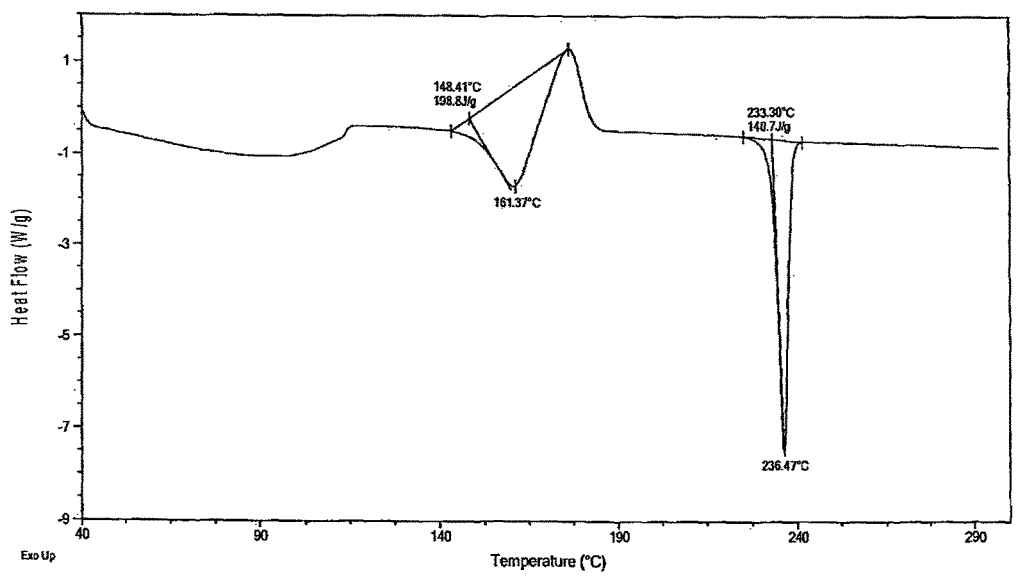
FIG. 6: Illustrates the DSC thermogram of crystalline form-N of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1.

The sixth aspect of the present invention provides a novel crystalline form-N of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1, characterized by;
a) its PXRD pattern substantially in accordance with FIG. 5,
b) its powder X-ray diffractogram having peaks at 6.0, 7.1, 12.8, 13.6, 15.1, 15.6, 16.1, 16.4, 17.5, 19.1, 21.3, 21.6, 22.7 and 24.4±0.2 degrees of two-theta,
c) its DSC thermogram as illustrated in FIG. 6.

The sixth aspect of the present invention also provides a process for the preparation of crystalline form-N of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1, comprising the following steps of:
a) Adding a mixture of dichloromethane and ethyl acetate to 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1,
b) heating the reaction mixture,
c) cooling the reaction mixture,
d) filtering the compound and drying to get crystalline form-N of compound of formula-1.

The seventh aspect of the present invention provides a process for the preparation of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1, comprising of:

a) Reacting 4-iodoaniline compound of formula-2

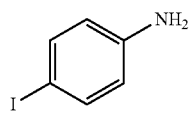

Formula-2 with 5-bromopentanoyl chloride in presence of a suitable base in a suitable solvent to provide 5-bromo-N-(4-iodophenyl)pentanamide compound of formula-3,

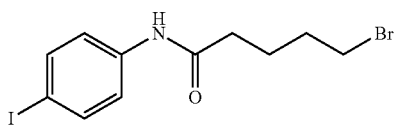

Formula-3 optionally isolating the compound of formula-3 as a solid, b) cyclizing the compound of formula-3 in presence of a suitable base in a suitable solvent to provide 1-(4-iodophenyl)piperidin-2-one compound of formula-4,

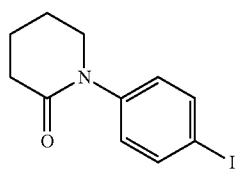

Formula-4 c) reacting the compound of formula-4 with phosphorous pentachloride in a suitable solvent to provide 3,3-dichloro-1-(4-iodophenyl)piperidin-2-one compound of formula-5,

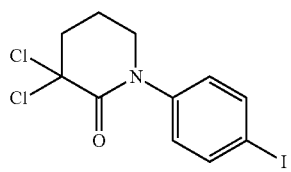

Formula-5 d) treating the compound of formula-5 with lithium carbonate in presence of alkali metal halide in a suitable solvent to provide 3-chloro-1-(4-iodophenyl)-5,6-dihydropyridin-2(1H)-one compound of formula-6,

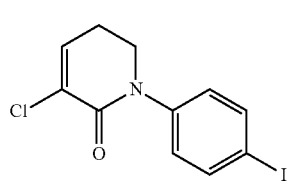

Formula-6 optionally purifying the compound of formula-6 using a suitable solvent, e) reacting the compound of formula-6 with morpholine in a suitable solvent to provide 1-(4-iodophenyl)-3-morpholino-5,6-dihydropyridin-2(1H)-one compound of formula-7,

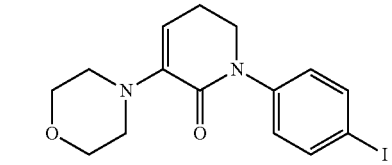

Formula-7 f) reacting the compound of formula-7 with piperidin-2-one in presence of copper iodide and a suitable base in a suitable solvent to provide 3-morpholino-1-(4-(2-oxopiperidin-1-yl)phenyl)-5,6-dihydropyridin-2(1H)-one compound of formula-8,

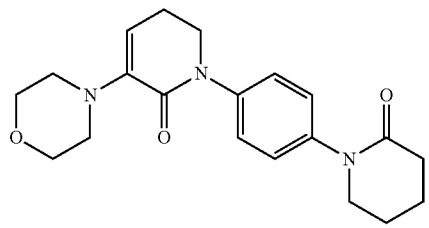

Formula-8 g) reacting 4-methoxyaniline compound of formula-12 with sodium nitrite in presence of conc. HCl in a suitable solvent, followed by reacting the obtained compound with ethyl-2-chloroacetoacetate in presence of sodium acetate in a suitable solvent to provide (Z)-ethyl 2-chloro-2-(2-(4-methoxyphenyl)hydrazono) acetate compound of formula-9, optionally purifying the compound of formula-9, h) condensing the compound of formula-8 with (Z)-ethyl 2-chloro-2-(2-(4-methoxyphenyl) hydrazono)acetate compound of formula-9 in presence of an inorganic base in a suitable solvent to provide ethyl 1-(4-methoxyphenyl)-7a-morpholino-7-oxo-6-(4-(2-oxopiperidin-1-yl)phenyl)-3a,4,5,6,7,7a-hexahydro-1H-pyrazolo[3,4-c]pyridine-3-carboxylate compound of formula-10,

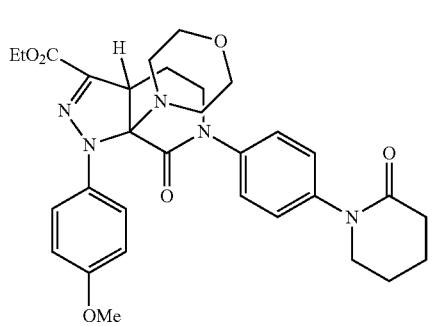

Formula-10 i) treating the compound of formula-10 in-situ with a suitable acid in a suitable solvent to provide ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate compound of formula-11,

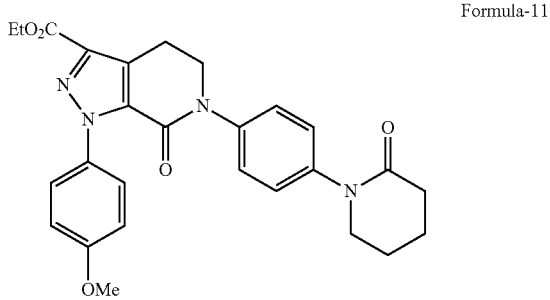 [SMILES: CCOC(=O)c1nn(-c2ccc(OC)cc2)c2c1CCN(c1ccc(N3CCCCC3=O)cc1)C2=O]

Formula-11 j) reacting the compound of formula-11 with formamide in presence of a suitable base in a suitable solvent to provide apixaban compound of formula-1,
k) optionally, purifying the compound of formula-1 in a suitable solvent to provide pure apixaban compound of formula-1.

In a preferred embodiment of the present invention provides a process for the preparation of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1, comprising of
 a) Reacting 4-iodoaniline compound of formula-2 with 5-bromopentanoyl chloride in presence of triethylamine in toluene to provide 5-bromo-N-(4-iodophenyl) pentanamide compound of formula-3 as a solid,
 b) cyclizing the compound of formula-3 in presence of sodium tertiary butoxide in toluene to provide 1-(4-iodophenyl)piperidin-2-one compound of formula-4,
 c) reacting the compound of formula-4 with phosphorous pentachloride in dichloromethane to provide 3,3-dichloro-1-(4-iodophenyl)piperidin-2-one compound of formula-5,
 d) treating the compound of formula-5 with lithium carbonate and sodium chloride in dimethylformamide to provide 3-chloro-1-(4-iodophenyl)-5,6-dihydropyridin-2(1H)-one compound of formula-6, further purifying the obtained compound using methanol to provide pure compound of formula-6,
 e) reacting the compound of formula-6 with morpholine in toluene to provide 1-(4-iodophenyl)-3-morpholino-5,6-dihydropyridin-2(1H)-one compound of formula-7,
 f) reacting the compound of formula-7 with piperidin-2-one in presence of copper iodide and potassium carbonate in o-xylene to provide 3-morpholino-1-(4-(2-oxopiperidin-1-yl)phenyl)-5,6-dihydropyridin-2(1H)-one compound of formula-8,
 g) reacting 4-methoxyaniline compound of formula-12 with sodium nitrite in presence of conc. HCl in water, followed by reacting the obtained compound with ethyl-2-chloroacetoacetate in presence of sodium acetate in a mixture of ethylacetate and water to provide (Z)-ethyl 2-chloro-2-(2-(4-methoxyphenyl)hydrazono)acetate compound of formula-9, further purifying the obtained compound using cyclohexane to provide pure compound of formula-9,
 h) condensing the compound of formula-8 with (Z)-ethyl 2-chloro-2-(2-(4-methoxy phenyl)hydrazono)acetate compound of formula-9 in presence of sodium carbonate in acetone to provide ethyl 1-(4-methoxyphenyl)-7a-morpholino-7-oxo-6-(4-(2-oxopiperidin-1-yl)phenyl)-3a,4,5,6,7,7a-hexahydro-1H-pyrazolo[3,4-c]pyridine-3-carboxylate compound of formula-10,
 i) treating the compound of formula-10 in-situ with dilute HCl to provide ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate compound of formula-11,
 j) reacting the compound of formula-11 with formamide in presence of sodium methoxide in isopropanol to provide apixaban compound of formula-1, further purifying the obtained compound using methanol,
 k) purifying the compound of formula-1 using dichloromethane and methanol followed by isopropanol to provide pure apixaban compound of formula-1.

The eighth aspect of the present invention is to provide a process for the preparation of ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate compound of formula-11, comprising of
 a) Condensing the compound of formula-8 with (Z)-ethyl 2-chloro-2-(2-(4-methoxyphenyl) hydrazono)acetate compound of formula-9 in presence of an inorganic base selected from alkali and alkaline earth metal hydroxides, alkoxides, carbonates and bicarbonates in a suitable solvent to provide ethyl 1-(4-methoxyphenyl)-7a-morpholino-7-oxo-6-(4-(2-oxopiperidin-1-yl)phenyl)-3a,4,5,6,7,7a-hexahydro-1H-pyrazolo[3,4-c]pyridine-3-carboxylate compound of formula-10,
 b) treating the compound of formula-10 in-situ with a suitable acid in a suitable solvent to provide ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate compound of formula-11.

In a preferred embodiment of the present invention provides a process for the preparation of ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate compound of formula-11, comprising of:
 c) Condensing the compound of formula-8 with (Z)-ethyl 2-chloro-2-(2-(4-methoxyphenyl) hydrazono)acetate compound of formula-9 in presence of sodium carbonate in acetone to provide ethyl 1-(4-methoxyphenyl)-7a-morpholino-7-oxo-6-(4-(2-oxopiperidin-1-yl)phenyl)-3a,4,5,6,7,7a-hexahydro-1H-pyrazolo[3,4-c]pyridine-3-carboxylate compound of formula-10,
 d) treating the compound of formula-10 in-situ with dilute HCl to provide ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate compound of formula-11.

The 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1 as produced by the present invention can be further micronized or milled to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.

The crystalline form-M, form-S and form-N of compound of formula-1 of the present invention are useful in the manufacture of pharmaceutical composition for the prevention of venous thromboembolism and venous thromboembolic events.

PXRD analysis of 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1 of the present invention was carried out using BRUKER/AXS X-ray diffractometer using Cu Kα radiation of wavelength 1.5406 A° at a continuous scan speed of 0.03°/min.

Differential scanning calorimetric (DSC) analysis was performed on a Q10 V9.6 Build 290 calorimeter with closed aluminium pans, heating the samples from 40 to 300° C. in a dry nitrogen atmosphere at a rate of 10° C./min.

HPLC Method of Analysis:

Apixaban compound of formula-1 of the present invention is analyzed by HPLC using the following conditions:

Apparatus: A liquid chromatographic system is to be equipped with variable wavelength UV-detector; Column: Zorbax Bonus RP, 250×4.6 mm, 5 μm or equivalent; Flow rate: 1.2 ml/min; wavelength: 270 nm; column temperature: 40° C.; Injection volume; 5 μL; Run time: 35 minutes; Needle wash: diluent; Diluent: Acetonitrile: water (90:10 v/v); Elution: Gradient; Mobile phase-A: Buffer; Mobile phase-B: acetonitrile:water (90:10 v/v); Buffer: Weigh accurately about 1.36 g of potassium dihydrogen ortho phosphate in 1000 10 ml of milli-Q water and adjust pH 6.0 with dil KOH solution, then filter through 0.22 μm nylon membrane filter paper.

The following impurities have been observed during the preparation of Apixaban.

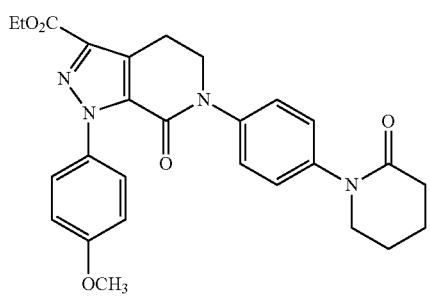

Ethylester Impurity

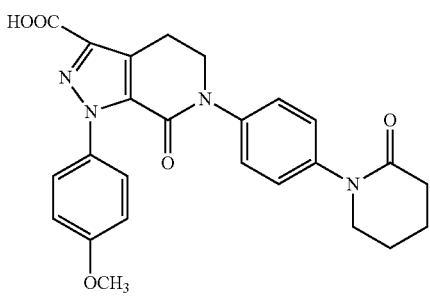

Acid Impurity

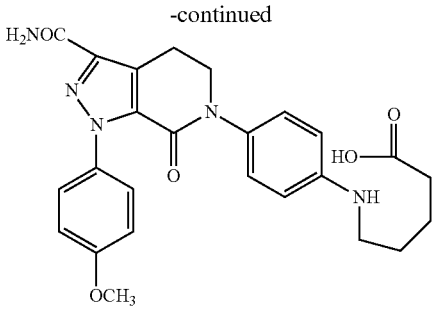

Aminoacid Impurity

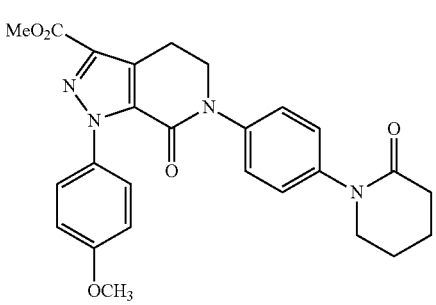

Methylester Impurity

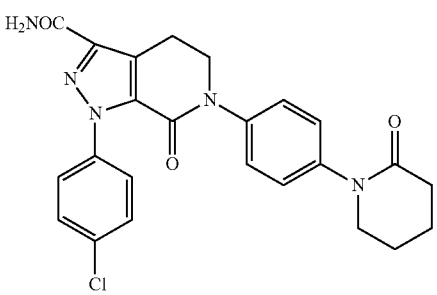

Chloro Impurity

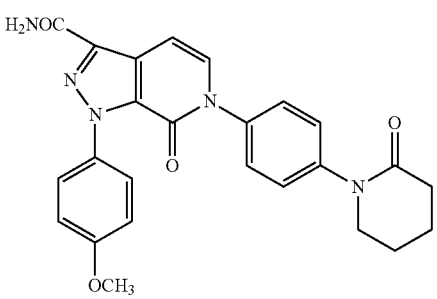

Dehydro Impurity

The present invention is schematically represented as follows.

Scheme-I:
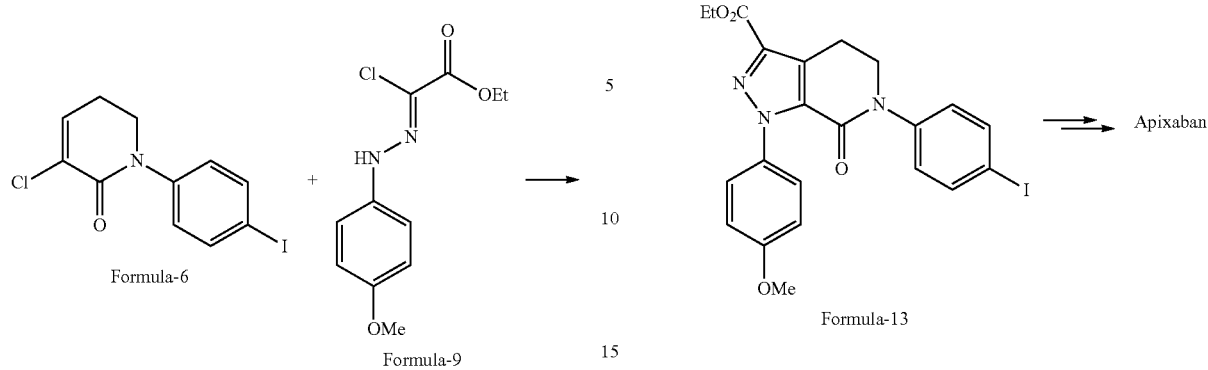
Scheme-II:
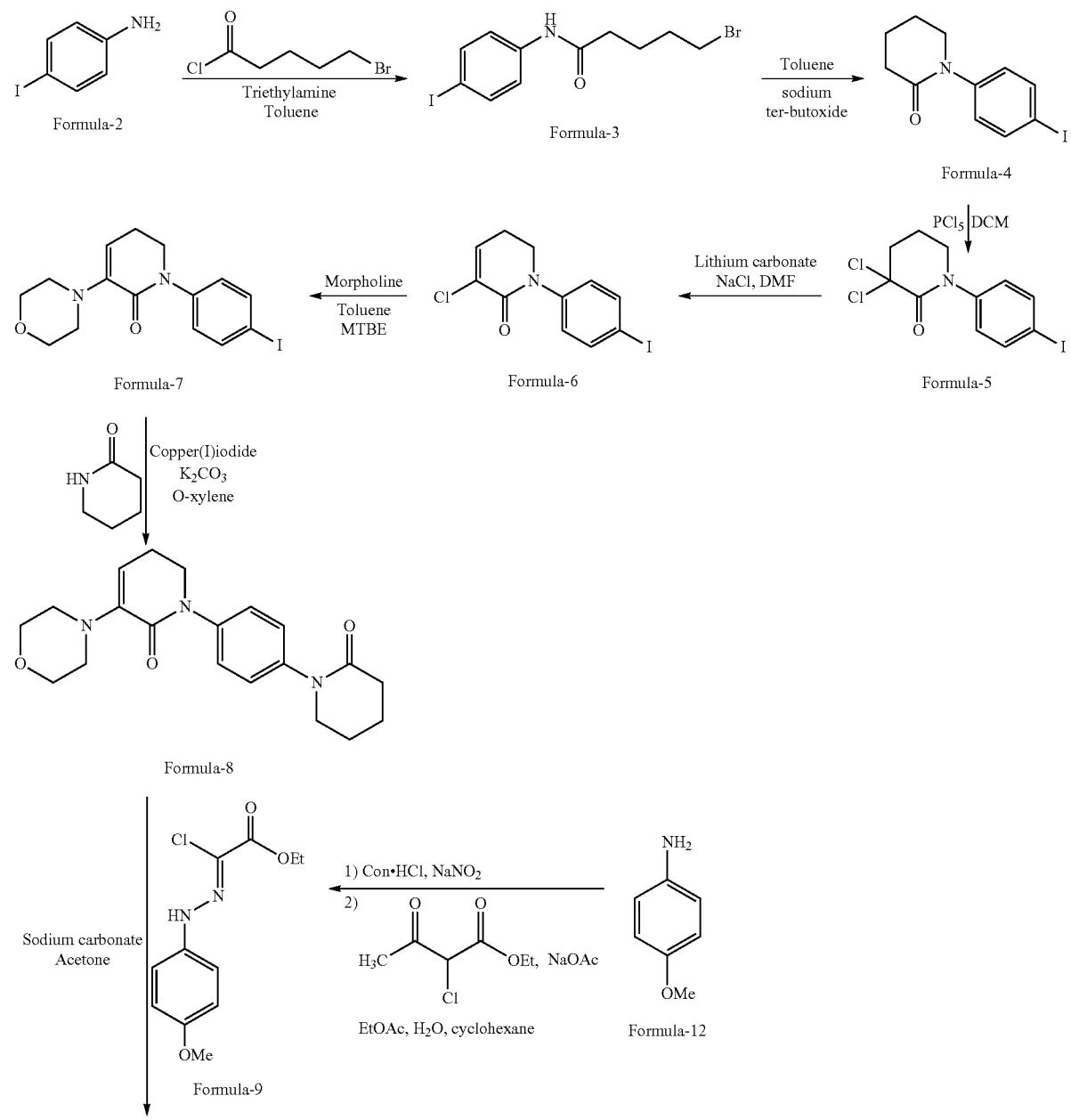

-continued

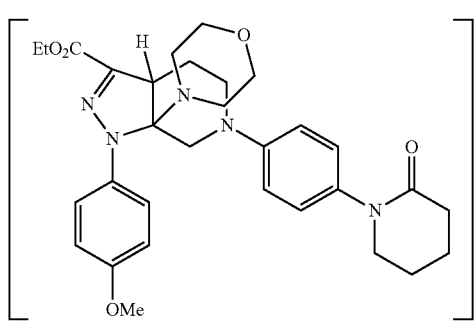

Formula-10

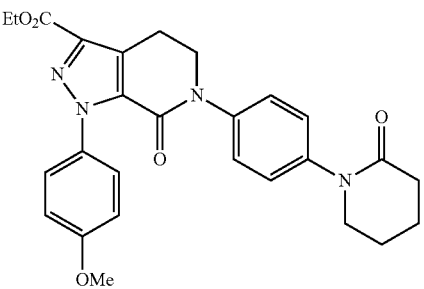

Formula-11

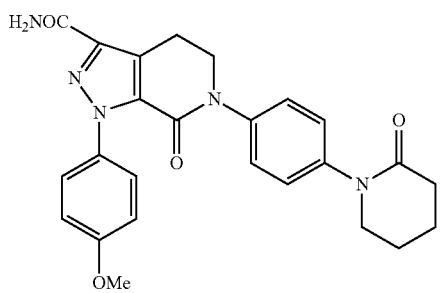

Pure Apixaban

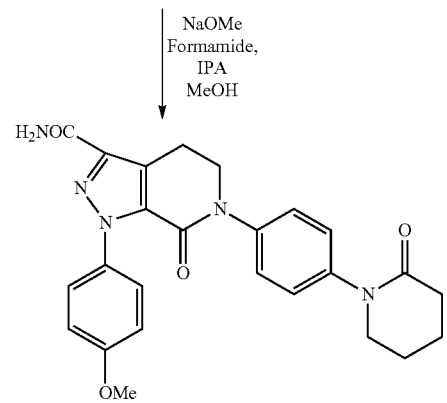

Formula-1
[Apixaban]

The process described in the present invention was demonstrated in examples illustrated below. These examples are provided as illustration only and therefore should not be construed as limitation of the scope of the invention.

EXAMPLES

Example-1: Preparation of 3-chloro-1-(4-iodophenyl)-5,6-dihydropyridin-2(1H)-one (Formula-6)

Lithium carbonate (4.08 gm) followed by lithium chloride (2.28 gm) were added to a mixture of 3,3-dichloro-1-(4-iodophenyl)piperidin-2-one compound of formula-5 (30 gm) and dimethylformamide (60 ml) at 25-30° C. and stirred for 5 min at the same temperature. Heated the reaction mixture to 110-115° C. and stirred for 4 hrs at the same temperature. Cooled the reaction mixture to 25-30° C. Water was added to the reaction mixture at 25-30° C. and stirred for 1 hr at the same temperature. Filtered the precipitated solid and then dried to get the title compound.
Yield: 25.0 gm; MR: 120-130° C.

Example-2: Preparation of 3-chloro-1-(4-iodophenyl)-5,6-dihydropyridin-2(1H)-one (Formula-6)

Lithium carbonate (2.99 gm) followed by sodium chloride (2.76 gm) were added to a mixture of 3,3-dichloro-1-(4-iodophenyl)piperidin-2-one compound of formula-5 (50 gm) and dimethylformamide (150 ml) at 30-35° C. and stirred for 10 min at the same temperature. Heated the reaction mixture to 110-115° C. and stirred for 6 hrs at the same temperature. Cooled the reaction mixture to 25-30° C. Water was added to the reaction mixture at 25-30° C. and stirred for 1 hr at the same temperature. Filtered the precipitated solid and then dried to get the title compound.
Yield: 42.0 gm; M.R: 120-130° C.

Example-3: Preparation of 1-(4-iodophenyl)-3-morpholino-5,6-dihydropyridin-2(1H)-one (Formula-7)

Morpholine (5.09 gm) was added to a mixture of 3-chloro-1-(4-iodophenyl)-5,6-dihydro pyridin-2(1H)-one compound of formula-6 (5 gm) and toluene (5 ml) at 25-30° C. and stirred for 5 min at the same temperature. Heated the reaction mixture to 115-120° C. and stirred for 3 hrs at the same temperature. Cooled the reaction mixture to 25-30° C. Water was added to the reaction mixture at 25-30° C. and stirred for 15 hrs at the same temperature. Filtered the precipitated solid and then dried to get the title compound.
Yield: 3.8 gm.

Example-4: Preparation of 1-(4-iodophenyl)-3-morpholino-5,6-dihydropyridin-2(1H)-one (Formula-7)

Morpholine (28.73 gm) was added to a mixture of 3-chloro-1-(4-iodophenyl)-5,6-dihydropyridin-2(1H)-one compound of formula-6 (50 gm) and toluene (50 ml) at 30-35° C. Heated the reaction mixture to 115-120° C. and stirred for 8 hrs at 115-120° C. After completion of the reaction, cooled the reaction mixture to 25-30° C. Methyl tert-butyl ether (100 ml) followed by water were slowly added to the reaction mixture at 25-30° C. Cooled the reaction mixture to 5-10° C. and stirred for 2 hours at 5-10° C. Filtered the precipitated solid and then dried to get the title compound. Yield: 45 gm.

Example-5: Preparation of ethyl 6-(4-iodophenyl)-1-(4-methoxyphenyl)-7-oxo-4,5,6,7-tetra hydro-1H-pyrazolo[3,4-c]pyridine-3-carboxylate (Formula-13)

A mixture of 3-chloro-1-(4-iodophenyl)-5,6-dihydropyridin-2(1H)-one compound of formula-6 (79.2 gm), (Z)-ethyl 2-chloro-2-(2-(4-methoxyphenyl)hydrazono)acetate compound of formula-9 (65 gm) and toluene (450 ml) was heated to 90-100° C. and stirred for 5 min at the same temperature. Triethyl amine (72 gm) was slowly added to the reaction mixture at 95-100° C. and stirred for 2½ hrs at the same temperature. Cooled the reaction mixture to 25-30° C. Water (110 ml) was added to the reaction mixture at 25-30° C. and stirred for 8 hrs at the same temperature. Filtered the solid, washed with water and then dried to get the title compound.
Yield: 78.5 gm.

Example-6: Preparation of 5-bromo-N-(4-iodophenyl)pentanamide (Formula-3)

A mixture of 5-bromopentanoic acid (54 g), thionyl chloride (41 g), dimethylformamide (2 ml) and toluene (100 ml) was heated to 40-45° C. and stirred for 2 hours at the same temperature. Distilled off the reaction mixture to remove the un-reacted thionyl chloride under reduced pressure at a temperature below 40° C. Toluene (50 ml) was added to the reaction mixture and stirred for 15 minutes. The reaction mixture was cooled to 25-30° C. under nitrogen atmosphere and it slowly added to a pre-cooled mixture of 4-iodoaniline compound of formula-2 (50 g) and toluene (350 ml) at 0-5° C. Triethyl amine (29 g) was added to it at 0-5° C. The above reaction mixture containing acid chloride was slowly added to the reaction mixture containing 4-iodoaniline under nitrogen atmosphere and stirred for 2 hours at 0-5° C. Water (250 ml) was added to the reaction mixture and stirred for 2 hours at 0-5° C. Filtered the precipitated solid and then dried to get title compound. Yield: 83 gm; MR: 135-140° C.; HPLC purity: 99%.

Example-7: Preparation of 3-chloro-1-(4-iodophenyl)-5,6-dihydropyridin-2(1H)-one (Formula-6)

Step-a) Preparation of 1-(4-iodophenyl)piperidin-2-one (Formula-4)

Sodium tert-butoxide (18.86 g) was added to a mixture of 5-bromo-N-(4-iodophenyl)pentanamide compound of formula-3 (50 g) and toluene (250 ml) at 0-5° C. and stirred for 2 hours at 0-5° C. Water (100 ml) followed by aqueous hydrochloric acid solution (50 ml) were added to the reaction mixture and stirred for 10 minutes at 5-10° C. Both the organic and aqueous layers were separated; the organic layer was washed with water. Distilled off the solvent from the organic layer under reduced pressure at a temperature below 60° C. to get title compound as a solid.

Step-b) Preparation of 3,3-dichloro-1-(4-iodophenyl)piperidin-2-one (Formula-5)

The compound obtained in step-a) was dissolved in dichloromethane (100 ml) and slowly added to a mixture of phosphorous pentachloride (95 g) and dichloromethane (150 ml) at 25-30° C. The reaction mixture was heated to 35-40° C. and stirred for 4 hours at the same temperature. Cooled the reaction mixture to 5-10° C. Chilled water (150 ml) was added to the reaction mixture and stirred for 1.5 hours at 10-15° C. Both the organic and aqueous layers were separated; the organic layer was washed with water followed by 10% aqueous sodium carbonate solution. Distilled off the solvent completely from the organic layer to get title compound as a solid.

Step-c) Preparation of 3-chloro-1-(4-iodophenyl)-5,6-dihydropyridin-2(1H)-one (Formula-6)

To the obtained compound in step-b), dimethylformamide (100 ml), followed by lithium carbonate (2.2 g) and sodium chloride (2.0 g) were added at 25-30° C. The reaction mixture was heated to 115-120° C. and stirred for 6 hours at the same temperature. Cooled the reaction mixture to 30-35° C., water (350 ml) was added to it and stirred for 2 hours at 25-30° C. Filtered the precipitated solid and washed with water. Methanol (360 ml) was added to the obtained solid and the reaction mixture was heated to 65-70° C. Stirred the reaction mixture for 20 minutes at the same temperature. Carbon (3.0 g) was added to the reaction mixture and stirred for 20 minutes at 65-70° C. Filtered the reaction mixture through hyflow bed and washed with methanol. Distilled off the solvent from the filtrate under reduced pressure and methanol (300 ml) was added to the residue and stirred for 20 minutes at 25-30° C. Cooled the reaction mixture to −5 to 0° C. and stirred for 60 minutes at the same temperature. Filtered the precipitated solid, washed with methanol and then dried to get title compound.
Yield: 25 gm; MR: 115-120° C.: HPLC purity: 98%.

Example-8: Preparation of 3-morpholino-1-(4-(2-oxopiperidin-1-yl)phenyl)-5,6-dihydropyridin-2(1H)-one (Formula-8)

A mixture of 1-(4-iodophenyl)-3-morpholino-5,6-dihydropyridin-2(1H)-one compound of formula-7 (50 g), piperidin-2-one (32.25 g) and o-xylene (75 ml) was stirred for 10 minutes at 25-30° C. Potassium carbonate (27.0 g), followed by copper iodide (7.43 g) were added to the reaction mixture. The reaction mixture was heated to 140-145° C. under azeotropic distillation condition and stirred for 6 hours at the same temperature. Cooled the reaction mixture to 35-40° C., water (175 ml) was slowly added to the reaction mixture at 35-40° C. Cooled the reaction mixture to 10-15° C. and ammonia (125 ml) was added to the reaction mixture at 10-15° C. The temperature of the reaction mixture was raised to 25-30° C. and stirred for 2 hours at the same temperature. Filtered the precipitated solid, washed with water and then dried to get title compound.
Yield: 35 gm; MR: 195-200° C.; HPLC purity: 95%.

Example-9: Preparation of (Z)-ethyl 2-chloro-2-(2-(4-methoxyphenyl)hydrazono)acetate (Formula-9)

A mixture of 4-methoxyaniline compound of formula-12 (50 g) and water (150 ml) was cooled to 5-10° C. Hydrochloric acid (100 ml), followed by a solution of sodium nitrite (30.81 g) in water (50 ml) were slowly added to the reaction mixture at 5-10° C. and stirred for 2 hours at 5-10° C. to provide diazotized compound. Ethyl acetate (250 ml) was added to the reaction mixture. Ethyl 2-chloro acetoacetate (76.84 g) was slowly added to a mixture of sodium acetate (76.6 g), ethyl acetate (250 ml) and water (150 ml) at 25-30° C. and the reaction mixture was stirred for 2 hours at 25-30° C. The reaction mixture was slowly added to the reaction mixture containing diazotized compound at a temperature below 10° C. The temperature of the reaction mixture was raised to 25-30° C. and stirred for 16 hours at the same temperature. Both the organic and aqueous layers were separated and the organic layer was washed with 10% aqueous sodium bicarbonate solution followed by 10% aqueous sodium chloride solution. Distilled off the solvent completely from the organic layer under reduced pressure and then co-distilled with toluene. Toluene was added to the obtained compound and stirred for 15 minutes at 25-30° C. Silica-gel was added to the reaction mixture and stirred for 30 minutes at 25-30° C. Filtered the reaction mixture and the solvent from the filtrate was distilled off completely under reduced pressure. Cyclohexane (400 ml) was added to the obtained compound and the reaction mixture was stirred for 60 minutes at 25-30° C. Filtered the precipitated solid, washed with cyclohexane and then dried to get title compound. Yield: 60 gm; MR: 95-100° C.; HPLC purity: 99%.

Example-10: Preparation of ethyl 1-(4-methoxyphenyl)-7-oxo-6-(4-(2-oxopiperidin-1-yl) phenyl)-4,5,6,7-tetrahydro-1H-pyrazolo[3,4-c]pyridine-3-carboxylate (Formula-11)

A mixture of 3-morpholino-1-(4-(2-oxopiperidin-1-yl)phenyl)-5,6-dihydropyridin-2(1H)-one compound of formula-8 (30 g), sodium carbonate (26.83 g) and acetone (150 ml) was heated to 45-50° C. (Z)-ethyl 2-chloro-2-(2-(4-methoxyphenyl)hydrazono)acetate compound of formula-9 (32.5 g) was added to the reaction mixture at 45-50° C. and stirred for 3 hours at the same temperature. Cooled the reaction mixture to 25-30° C. and aqueous hydrochloric acid (50 ml) in 50 ml of water was added to it at 25-30° C. Stirred the reaction mixture for 2 hours at 25-30° C. Water was slowly added to the reaction mixture and stirred for 45 minutes at 25-30° C. Filtered the obtained solid and washed with water. The obtained solid was recrystallized from toluene (150 ml) to get the title compound. Yield: 35 gm; MR: 155-160° C.; HPLC purity: 97%.

Example-11: Preparation of 1-(4-methoxyphenyl)-7-oxo-6-[4-(2-oxo piperidin-1-yl)phenyl]-4,5,6,7-tetrahydro-1H-pyrazolo[3,4-c]pyridine-3-carboxamide (Formula-1)

A mixture of ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate compound of formula-11 (50 g), formamide (150 ml), sodium methoxide (30 ml) and isopropanol (300 ml) was heated to 65-70° C. and stirred for 2 hours at 65-70° C. Cooled the reaction mixture to 0-5° C. and stirred for 30 minutes at 0-5° C. Filtered the precipitated solid and washed with isopropanol. Methanol (150 ml) was added to the obtained solid, the reaction mixture was heated to 65-70° C. and stirred for 15 minutes at 65-70° C. Cooled the reaction mixture to 0-5° C. and stirred for 30 minutes at 0-5° C. Filtered the precipitated solid, washed with methanol and then dried to get title compound. Yield: 35 g. MR: 230-235° C.; HPLC purity: 98%.

The PXRD of the crystalline solid obtained from the above example is matches with the PXRD of crystalline form-M of the present invention.

Example-12: Purification of 1-(4-methoxyphenyl)-7-oxo-6-[4-(2-oxo piperidin-1-yl)phenyl]-4,5,6,7-tetrahydro-1H-pyrazolo[3,4-c]pyridine-3-carboxamide (Formula-1)

1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1 (100 g) was dissolved in a mixture of dichloromethane (1200 ml) and methanol (200 ml) at 25-30° C. 10% aqueous sodium carbonate solution (200 ml) was added to the reaction mixture and stirred for 15 minutes at 25-30° C. Both the organic and aqueous layers were separated, methanol (100 ml) was added to the organic layer and again 200 ml of 10% aqueous sodium carbonate solution was added to the reaction mixture. The reaction mixture was stirred for 15 minutes at 25-30° C. and separated the organic and aqueous layers. To the organic layer methanol (100 ml) followed by water (200 ml) were added. Both the organic and aqueous layers were separated. The solvent from organic layer was distilled under reduced pressure at a temperature below 40° C. 3000 ml of a mixture of dichloromethane and methanol (in the ratio of 3:7) was added to the crude compound and the reaction mixture was heated to reflux temperature and stirred for 10 minutes. Carbon (10 g) was added to the reaction mixture and stirred for 15 minutes at the reflux temperature. Filtered the reaction mixture through hyflow bed, washed with a mixture of dichloromethane and methanol. The filtrate was cooled to 0-5° C. and stirred for 2 hours at 0-5° C. Filtered the precipitated solid and washed with a mixture of dichloromethane and methanol. Isopropanol (1000 ml) was added to the reaction mixture. Heated the reaction mixture to 80-85° C. and stirred for 15 minutes. Cooled the reaction mixture to 25-30° C. and stirred for 2 hours at 35-30° C. Filtered the precipitated solid, washed with isopropanol and then dried to get title compound.

Yield: 80 gm; MR: 235-240° C.

The PXRD pattern of crystalline solid obtained from the above example is matches with PXRD of crystalline form-M of the present invention.

Example-13: Preparation of crystalline form-M of 1-(4-methoxyphenyl)-7-oxo-6-[4-(2-oxo piperidin-1-yl)phenyl]-4,5,6,7-tetrahydro-1H-pyrazolo[3,4-c]pyridine-3-carboxamide (Formula-1)

1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1 (6.25 gm) was added to isopropanol (400 ml) at 25-30° C. Heated the reaction mixture to reflux temperature and stirred for 15 min at the same temperature. Cooled the reaction mixture to 0-5° C. and stirred for 60 min the same temperature. Filtered the solid, washed with isopropanol and then dried to get the title compound. Yield: 4.5 gm; Water content: 0.30% w/w. HPLC purity: 99.8%; Acid impurity: 0.02%; Amino acid impurity: Not detected; Chloro impurity: 0.01%; Methyl ester impurity: 0.05%; Ethyl ester impurity: 0.01%; Dehydro impurity: 0.07%.

Particle size distribution: D(0.1): 9.183 μm; D(0.5): 25.991 μm; D(0.9): 60.749 μm; D[4,3]: 31.066 μm.

The PXRD and DSC of the obtained compound are illustrated in FIG. 1 and FIG. 2 respectively.

Example-14: Preparation of crystalline form-M of 1-(4-methoxyphenyl)-7-oxo-6-[4-(2-oxo piperidin-1-yl)phenyl]-4,5,6,7-tetrahydro-1H-pyrazolo[3,4-c]pyridine-3-carboxamide (Formula-1)

1-(4-methoxyphenyl)-7-oxo-6-[4-(2-oxopiperidin-1-yl)phenyl]-4,5,6,7-tetrahydro-1H-pyrazolo[3,4-c]pyridine-3- carboxamide compound of formula-1 (6.25 gm) was added to 50% aqueous isopropanol (60 ml) at 25-30° C. Heated the reaction mixture to 50-60° C. and stirred for 4 hrs at the same temperature. Cooled the reaction mixture to 25-30° C. and stirred for 60 min at the same temperature. Filtered the solid and then dried to get the title compound.

Yield: 4.1 gm; Water content: 0.35% w/w.

The PXRD and DSC of the obtained compound are illustrated in FIG. 1 and FIG. 2 respectively.

Example-15: Preparation of crystalline form-S of 1-(4-methoxyphenyl)-7-oxo-6-[4-(2-oxo piperidin-1-yl)phenyl]-4,5,6,7-tetrahydro-1H-pyrazolo[3,4-c]pyridine-3-carboxamide (Formula-1)

1-(4-methoxyphenyl)-7-oxo-6-[4-(2-oxopiperidin-1-yl) phenyl]-4,5,6,7-tetrahydro-1H-pyrazolo[3,4-c]pyridine-3-carboxamide compound of formula-1 (34 gm) was added to a mixture of dichloromethane and methanol at 25-30° C. Heated the reaction mixture to reflux temperature and stirred for 15 min at the same temperature. Filtered the reaction mixture and washed with a mixture of dichloromethane and methanol. Cooled the filtrate to 0-5° C. and stirred for 60 min at the same temperature. Filtered the precipitated solid and then dried to get the title compound.

Yield: 24.0 gm; M.R: 235-245° C.; Water content: 7.38% w/w.

The PXRD and DSC of the obtained compound are illustrated in FIG. 3 and FIG. 4 respectively.

Example-16: Preparation of crystalline form-N of 1-(4-methoxyphenyl)-7-oxo-6-[4-(2-oxo piperidin-1-yl)phenyl]-4,5,6,7-tetrahydro-1H-pyrazolo[3,4-c]pyridine-3-carboxamide (Formula-1)

A mixture of dichloromethane and ethyl acetate (625 ml, in 3:7 ratio) was added to 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide compound of formula-1 (6.25 gm) at 25-30° C. Heated the reaction mixture to reflux temperature and stirred for 15 min at the same temperature. Cooled the reaction mixture to 0-5° C. and stirred for 60 min at the same temperature. Filtered the solid and then dried to get title compound. Yield: 3.9 g; Water content: 5.21% w/w.

The PXRD and DSC of the obtained compound are illustrated in FIG. 5 and FIG. 6 respectively.

Example-17: Preparation of crystalline form-M of 1-(4-methoxyphenyl)-7-oxo-6-[4-(2-oxo piperidin-1-yl)phenyl]-4,5,6,7-tetrahydro-1H-pyrazolo[3,4-c]pyridine-3-carboxamide (Formula-1)

1-(4-methoxyphenyl)-7-oxo-6-[4-(2-oxopiperidin-1-yl) phenyl]-4,5,6,7-tetrahydro-1H-pyrazolo[3,4-c]pyridine-3-carboxamide compound of formula-1 (34 gm) was added to a mixture of dichloromethane and methanol (1020 ml, in 3:7 ratio) at 25-30° C. Heated the reaction mixture to reflux temperature and stirred for 15 min at the same temperature. Filtered the reaction mixture and washed with a mixture of dichloromethane and methanol. Cooled the filtrate to 0-5° C. and stirred for 60 min at the same temperature. Filtered the precipitated solid and added to isopropanol (510 ml). Heated the reaction mixture to reflux temperature and stirred for 15 Minutes at the same temperature. The reaction mixture was cooled to 0-5° C. and stirred for 60 minutes at the same temperature. Filtered the solid and then dried to get crystalline form-M of compound of formula-1.

Yield: 23 g; Water content: 0.30% w/w.

The PXRD and DSC of the obtained compound are illustrated in FIG. 1 and FIG. 2 respectively.

Example-18: Preparation of crystalline form-M of 1-(4-methoxyphenyl)-7-oxo-6-[4-(2-oxo piperidin-1-yl)phenyl]-4,5,6,7-tetrahydro-1H-pyrazolo[3,4-c]pyridine-3-carboxamide (Formula-1)

1-(4-methoxyphenyl)-7-oxo-6-[4-(2-oxopiperidin-1-yl) phenyl]-4,5,6,7-tetrahydro-1H-pyrazolo[3,4-c]pyridine-3-carboxamide compound of formula-1 (34 gm) was added to a mixture of dichloromethane and methanol (1020 ml, in 3:7 ratio) at 25-30° C. Heated the reaction mixture to reflux temperature and stirred for 15 min at the same temperature. Filtered the reaction mixture and washed with a mixture of dichloromethane and methanol. Cooled the filtrate to 0-5° C. and stirred for 60 min at the same temperature. Filtered the precipitated solid and added to aq.isopropanol (340 ml). Heated the reaction mixture to 50-60° C. and stirred for 15 minutes at the same temperature. The reaction mixture was cooled to 25-35° C. and stirred for 60 minutes at the same temperature. Filtered the solid and then dried to get crystalline form-M of compound of formula-1.

Yield: 23 g; Water content: 0.35% w/w.

The PXRD and DSC of the obtained compound are illustrated in FIG. 1 and FIG. 2 respectively.

We claim:

1. A process for the preparation of 1-(4-methoxyphenyl)-7-oxo-6-[4-(2-oxopiperidin-1-yl) phenyl]-4,5,6,7-tetrahydro-1H-pyrazolo[3,4-c]pyridine-3-carboxamide compound of formula-1, comprising:

a) reacting 4-iodoaniline compound of formula-2

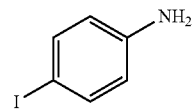

Formula-2 with 5-bromopentanoyl chloride in presence of triethylamine in toluene to provide 5-bromo-N-(4-iodophenyl)pentanamide compound of formula-3 as a solid,

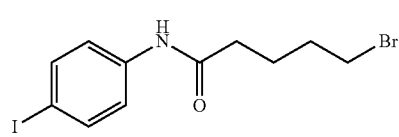

Formula-3 b) cyclizing the compound of formula-3 in presence of sodium tertiary butoxide in toluene to provide 1-(4-iodophenyl)piperidin-2-one compound of formula-4,

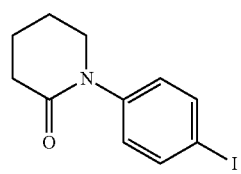

Formula-4 c) reacting the compound of formula-4 with phosphorous pentachloride in dichloromethane to provide 3,3-dichloro-1-(4-iodophenyl)piperidin-2-one compound of formula-5, Formula-5

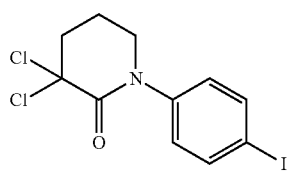

d) treating the compound of formula-5 with lithium carbonate and sodium chloride in dimethylformamide to provide 3-chloro-1-(4-iodophenyl)-5,6-dihydropyridin-2(1H)-one compound of formula-6, further purifying the obtained compound using methanol to provide pure compound of formula-6, Formula-6

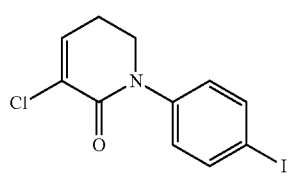

e) reacting the compound of formula-6 with morpholine in toluene to provide 1-(4-iodophenyl)-3-morpholino-5,6-dihydropyridin-2(1H)-one compound of formula-7, Formula-7

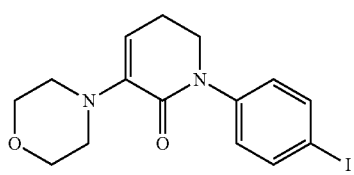

f) reacting the compound of formula-7 with piperidin-2-one in presence of copper iodide and potassium carbonate in o-xylene to provide 3-morpholino-1-(4-(2-oxopiperidin-1-yl)phenyl)-5,6-dihydropyridin-2(1H)-one compound of formula-8, Formula-8

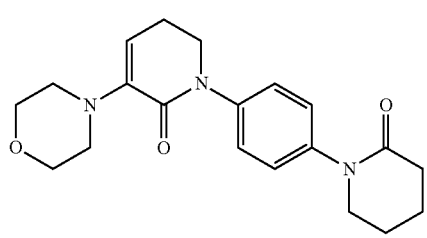

g) condensing the compound of formula-8 with (Z)-ethyl 2-chloro-2-(2-(4-methoxyphenyl) hydrazono)acetate compound of formula-9 in presence of sodium carbonate in acetone to provide ethyl 1-(4-methoxyphenyl)-7a-morpholino-7-oxo-6-(4-(2-oxopiperidin-1-yl) phenyl)-3a,4,5,6,7,7a-hexahydro-1H-pyrazolo[3,4-c]pyridine-3-carboxylate compound of formula-10, Formula-10

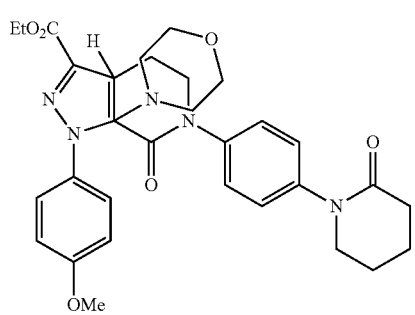

h) treating the compound of formula-10 in-situ with dilute HCl to provide ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate compound of formula-11, Formula-11

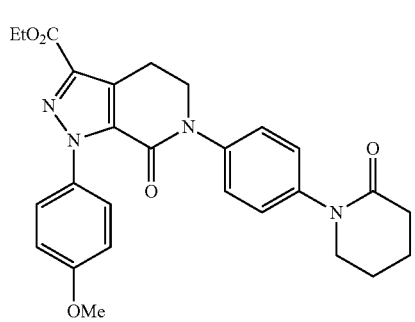

i) reacting the compound of formula-11 with formamide in presence of sodium methoxide in isopropanol to provide apixaban compound of formula-1, optionally purifying the compound with methanol to provide pure compound of formula-1, and j) purifying the compound of formula-1 using dichloromethane and methanol followed by isopropanol to provide pure apixaban compound of formula-1.

2. The process according to claim 1, wherein, the compound of formula-6

Formula-6

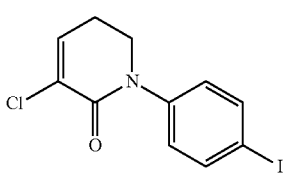

is prepared by the process comprising treating the 3,3-dichloro-1-(4-iodophenyl) piperidin-2-one compound of formula-5

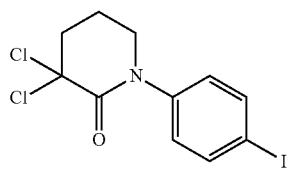

Formula-5

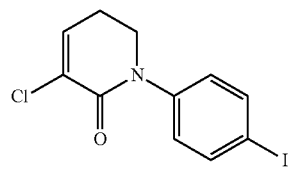 [SMILES: O=C1C(Cl)=CCCN1c1ccc(I)cc1]

Formula-6 with lithium carbonate in presence of an alkali metal halide such as lithium chloride and sodium chloride in a solvent at a temperature to provide 3-chloro-1-(4-iodophenyl)-5,6-dihydropyridin-2(1H)-one compound of formula-6.

3. The process according to claim 2, wherein the solvent is selected from hydrocarbon solvents, chloro solvents, ester solvents, ether solvents, alcoholic solvents, ketone solvents, polar aprotic solvents, polar solvents or mixtures thereof, preferably polar aprotic solvents.

4. The process according to claim 2, wherein, lithium carbonate and alkali metal halide are employed individually in molar proportions ranging from 0.2 to 1 equivalents per one mole of compound of formula-5; the solvent is employed in an amount ranging from 2 to 10 volumes per 1 gm of compound of formula-5; and the temperature ranges from 0° C. to 130° C.

5. The process according to claim 2, wherein the compound of formula-6,

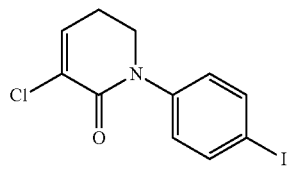

Formula-6 is prepared by the process comprising treating the 3,3-dichloro-1-(4-iodophenyl) piperidin-2-one compound of formula-5,

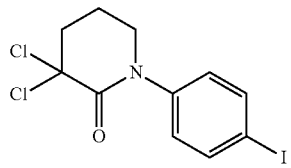

Formula-5 with lithium carbonate in the presence of sodium chloride in N,N-dimethyl formamide at 100° C. to 125° C. to provide 3-chloro-1-(4-iodophenyl)-5,6-dihydropyridin-2(1H)-one compound of formula-6.

6. The process according to claim 2, wherein the compound of formula-6, is prepared by the process comprising treating the 3,3-dichloro-1-(4-iodophenyl) piperidin-2-one compound of formula-5,

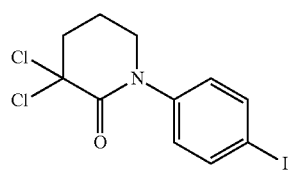

Formula-5 with lithium carbonate in the presence of lithium chloride in N,N-dimethyl formamide at 100° C. to 125° C. to provide 3-chloro-1-(4-iodophenyl)-5,6-dihydropyridin-2(1H)-one compound of formula-6.

7. The process according to claim 1, wherein the compound of formula-7,

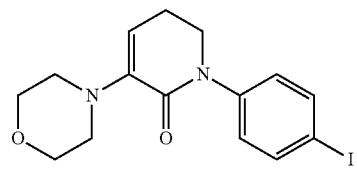

Formula-7 is prepared by the process comprising reacting the 3-chloro-1-(4-iodophenyl)-5,6-dihydropyridin-2(1H)-one compound of formula-6 with morpholine in the presence or absence of a solvent selected from hydrocarbon solvents, chloro solvents, ester solvents, ether solvents, alcoholic solvents, ketone solvents, polar aprotic solvents, polar solvents or mixtures thereof, preferably hydrocarbon solvents and ether solvents at a temperature to provide 1-(4-iodophenyl)-3-morpholino-5,6-dihydropyridin-2(1H)-one compound of formula-7.

8. The process according to claim 7, wherein, the morpholine is employed in molar proportions ranging from 1 to 10 equivalents per one mole of compound of formula-6 the solvent is employed in an amount ranging from 1 to 10 volumes per 1 gm of compound of formula-6; and the temperature is 0° C. to 140° C.

9. The process according to claim 1, wherein the compound of formula-13,

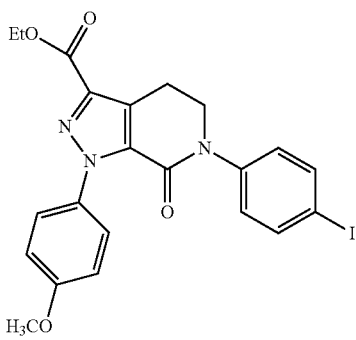

Formula-13 is prepared by the process comprising reacting the chloro-1-(4-iodophenyl)-5,6-dihydropyridin-2(1H)-one compound of formula-6 with (Z)-ethyl 2-chloro-2-(2-(4-methoxyphenyl) hydrazono) acetate compound of formula-9

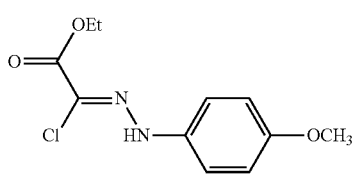

Formula-9 in presence of an organic base in a solvent selected from hydrocarbon solvents, chloro solvents, ester solvents, ether solvents, alcoholic solvents, ketone solvents, polar aprotic solvents, polar solvents and/or mixtures thereof, preferably hydrocarbon solvents and ester solvents at a temperature to provide 6-(4-iodophenyl)-1-(4-methoxyphenyl)-7-oxo-4,5,6,7-tetrahydro-1H-pyrazolo[3,4-c]pyridine-3-carboxylate compound of formula-13.

10. The process according to claim 9, wherein, the base is employed in molar proportions ranging from 1 to 3 equivalents per one mole of compound of formula-6; the solvent is used in an amount ranging from 2 to 10 volumes per 1 gm of compound of formula-6; and the temperature ranges from 0° C. to 100° C.

11. The process according to claim 1, wherein, the compound of formula-1 is prepared by the process comprising:
(a) preparing the compound of formula-6 according to claim 6,
(b) reacting the compound of formula-6 with morpholine in toluene to provide 1-(4-iodophenyl)-3-morpholino-5,6-dihydropyridin-2(1H)-one compound of formula-7,
(c) reacting the compound of formula-7 with piperidin-2-one in presence of copper iodide and potassium carbonate in o-xylene to provide 3-morpholino-1-(4-(2-oxopiperidin-1-yl)phenyl)-5,6-dihydropyridin-2(1H)-one compound of formula-8,
(d) condensing the compound of formula-8 with (Z)-ethyl 2-chloro-2-(2-(4-methoxyphenyl) hydrazono)acetate compound of formula-9 in the presence of sodium carbonate in acetone to provide ethyl 1-(4-methoxyphenyl)-7a-morpholino-7-oxo-6-(4-(2-oxopiperidin-1-yl) phenyl)-3a,4,5,6,7,7a-hexahydro-1H-pyrazolo[3,4-c]pyridine-3-carboxylate compound of formula-10,
(e) treating the compound of formula-10 in-situ with dilute HCl to provide ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate compound of formula-11,
(f) reacting the compound of formula-11 with formamide in the presence of sodium methoxide in isopropanol to provide apixaban compound of formula-1, optionally purifying the compound with methanol to provide pure compound of formula-1, and
(g) purifying the compound of formula-1 using dichloromethane and methanol followed by isopropanol to provide pure apixaban compound of formula-1.

12. The process according to claim 1, wherein, the (Z)-ethyl 2-chloro-2-(2-(4-methoxyphenyl) hydrazono)acetate compound of formula-9 can be prepared by the following steps of:
(a) reacting 4-methoxyaniline compound of formula-12 with sodium nitrite in presence of conc. HCl in water, followed by reacting with ethyl-2-chloroacetoacetate in presence of sodium acetate in a mixture of ethylacetate and water to provide (Z)-ethyl 2-chloro-2-(2-(4-methoxyphenyl)hydrazono)acetate compound of formula-9, and
(b) isolating the compound using cyclohexane to provide (Z)-ethyl 2-chloro-2-(2-(4-methoxyphenyl)hydrazono) acetate compound of formula-9 as a solid.

13. The process according to claim 1, wherein the compound of formula-11 is prepared by the process comprising:
a) condensing the compound of formula-8 with (Z)-ethyl 2-chloro-2-(2-(4-methoxyphenyl) hydrazono)acetate compound of formula-9 in presence of an inorganic base selected from alkali and alkaline earth metal hydroxides, alkoxides, carbonates and bicarbonates in a suitable solvent to provide ethyl 1-(4-methoxyphenyl)-7a-morpholino-7-oxo-6-(4-(2-oxopiperidin-1-yl)phenyl)-3a,4,5,6,7,7a-hexahydro-1H-pyrazolo[3,4-c]pyridine-3-carboxylate compound of formula-10, and
b) treating the compound of formula-10 in-situ with an acid in a solvent to provide ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate compound of formula-11.

14. The process according to claim 11, wherein, the (Z)-ethyl 2-chloro-2-(2-(4-methoxyphenyl) hydrazono)acetate compound of formula-9 can be prepared by the following steps of:
a) reacting 4-methoxyaniline compound of formula-12 with sodium nitrite in presence of concentrated HCl in water, followed by reacting with ethyl-2-chloroacetoacetate in presence of sodium acetate in a mixture of ethylacetate and water to provide (Z)-ethyl 2-chloro-2-(2-(4-methoxyphenyl)hydrazono)acetate compound of formula-9, and
b) isolating the compound using cyclohexane to provide (Z)-ethyl 2-chloro-2-(2-(4-methoxyphenyl)hydrazono) acetate compound of formula-9 as a solid.

15. 3-chloro-1-(4-iodophenyl)-5,6-dihydropyridin-2(1H)-one represented by the structural formula:

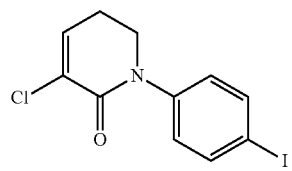

* * * * *